US012458796B2

(12) United States Patent
Lineaweaver

(10) Patent No.: US 12,458,796 B2
(45) **Date of Patent: *Nov. 4, 2025**

(54) RECIPIENT-DIRECTED ELECTRODE SET SELECTION

(71) Applicant: Cochlear Limited, Macquarie University (AU)

(72) Inventor: Sean Lineaweaver, Gig Harbor, WA (US)

(73) Assignee: Cochlear Limited, Macquarie University (AU)

( * ) Notice: Subject to any disclaimer, the term of this patent is extended or adjusted under 35 U.S.C. 154(b) by 0 days.

This patent is subject to a terminal disclaimer.

(21) Appl. No.: 18/462,980

(22) Filed: Sep. 7, 2023

(65) Prior Publication Data

US 2023/0414933 A1 Dec. 28, 2023

Related U.S. Application Data

(63) Continuation of application No. 16/929,409, filed on Jul. 15, 2020, now Pat. No. 11,786,724, which is a continuation of application No. 15/355,234, filed on Nov. 18, 2016, now Pat. No. 10,716,934.

(51) Int. Cl.
*A61N 1/00* (2006.01)
*A61N 1/05* (2006.01)
*A61N 1/36* (2006.01)
*A61N 1/372* (2006.01)

(52) U.S. Cl.
CPC ....... *A61N 1/0541* (2013.01); *A61N 1/36036* (2017.08); *A61N 1/36039* (2017.08); *A61N 1/37241* (2013.01)

(58) Field of Classification Search
CPC .......................... A61N 1/0541; A61N 1/36036
USPC ............................................................ 607/57
See application file for complete search history.

(56) References Cited

U.S. PATENT DOCUMENTS

| | | | |
|---|---|---|---|
| 7,908,012 | B2 | 3/2011 | Svirsky |
| 8,346,368 | B2 | 1/2013 | Killian |
| 8,565,889 | B2 | 10/2013 | Spitzer |
| 8,768,475 | B2 | 7/2014 | Litvak et al. |
| 8,880,180 | B2 | 11/2014 | van den Honert et al. |

(Continued)

FOREIGN PATENT DOCUMENTS

| | | |
|---|---|---|
| WO | 01/15773 A1 | 3/2001 |

OTHER PUBLICATIONS

Davis et al., "Relationship Between Electrode-to-Modiolus Distance and Current Levels for Adults With Cochlear mplants," otol Neurotol_ 37(1):31-7, 2016 {15 pages).

(Continued)

*Primary Examiner* — Nicole F Johnson
(74) *Attorney, Agent, or Firm* — Edell, Shapiro & Finnan, LLC

(57) ABSTRACT

Presented herein are techniques for the determination/selection of a set of electrodes for use in an electrically-stimulating auditory/hearing prosthesis. More specifically, an electrically-stimulating hearing prosthesis includes a plurality of electrodes implanted in a recipient. Based, at least in part on a recipient's subjective preferences, one or more of these electrodes may be deactivated. The remaining (i.e., non-deactivated) electrodes form a final electrode set that is subsequently used by the hearing prosthesis for subsequent hearing rehabilitation operations.

18 Claims, 7 Drawing Sheets

(56) References Cited

U.S. PATENT DOCUMENTS

| | | | |
|---|---|---|---|
| 9,067,069 B2 | 6/2015 | Svirsky | |
| 9,352,153 B2 | 5/2016 | van Dijk | |
| 2007/0293785 A1 | 12/2007 | Litvak | |
| 2008/0300653 A1 | 12/2008 | Svirsky | |
| 2009/0177246 A2 | 7/2009 | Svirsky | |
| 2011/0218592 A1 | 9/2011 | Svirsky | |
| 2013/0304157 A1* | 11/2013 | Smith | A61N 1/36038 607/57 |
| 2015/0025596 A1 | 1/2015 | Kals | |
| 2015/0045844 A1 | 2/2015 | Kulkarni | |
| 2015/0088225 A1 | 3/2015 | Noble et al. | |

OTHER PUBLICATIONS

Noble et al., "Clinical evaluation of an image-guided cochlear implant programming strategy," Audiol Neurootol. 19 (6):400-11, 2014 (22 pages).

Long et al., "Examining the electro-neural interface of cochlear implant users using psychophysics, CT scans, and speech understanding," J Assoc Res otolaryngol. Apr;15(2):293-304, 2014 (12 pages).

Bierer et al., "Identifying cochlear implant channels with poor electrode-neuron interface: partial tripolar, single-channel thresholds and psychophysical tuning curves," Ear Hear. v31 (2), 2010 {29 pages).

Bierer et al., "Identifying cochlear implant channels with poor electrode-neuron interfaces: electrically evoked auditory brain stem responses measured with the partial tripolar configuration," Ear Hear.v32(4), 2011 (19 pages)_.

Bierer, Julie and Litvak, Leonid, "Reducing Channel Interaction Through Cochlear Implant Programming May Improve Speech Perception: Current Focusing and Channel Deactivation," Trends in Hearing, vol. 20: 1-12, 2016 (12 pages).

J. Bierer, Ph. D, et al., "Identifying cochlear implant channels with poor electrode-neuron interface: partial tripolar, single-channel thresholds and psychophysical tuning curves" pubished in final edit form as: Ear Hear. Apr. 2010; 31(2): 247-258. doi:10.1097/AUD.Ob013e3181c7daf4, 29 pages.

J. Noble, et al., "Clinical Evaluation of an Image-Guided Cochlear Implant Programming Strategy", Audiology & Neurotology, Audio Neurotol 2014; 19: 400-411, Original Paper, DOI: 10 .1159/000365273, publishd on line Nov. 7, 2014, 12 pages.

C. Long, et al., "Examining the Electro-Neural Interface of Cochlear Implant Users Using Psychophysics, CT Scans, and Speech Understanding", Journal of the Association for Research in otolaryngology, JARO 15: 293-304 (2014), DOI: 10.1007/s10162-013-0437-5, Research Article, 12 pages.

J. Bierer, et al., "Identifying cochlear implant channels with poor electrode-neuron interfaces: electrically evoked auditory brain stem responses measured with the partial tripolar configuration", published in final edit form as: Ear Hear. 2011 ;32(4): 436-444. doi:10.1097/AUD.0b013e3181ff33ab, 19 pages.

T. David, et al., "Relationship Between Electrode-to-Modiolus Distance and Current Levels for Adults With Cochlear Implants", Otology & Neurotology, Jan. 2016, vol. 37, Issue 1, doi:10.1097/MAO.0000000000000896, Cochlear Implants, 7 pages.

International Search Report and Written Opinion in corresponding International Application No. PCT/IB2017/056963, mailed Feb. 13, 2018, 14 pages.

* cited by examiner

250

RECIPIENT-DIRECTED ELECTRODE SET SELECTION

CROSS REFERENCE TO RELATED APPLICATION

This application is a continuation of U.S. application Ser. No. 16/929,409, filed Jul. 2020, which is a continuation of U.S. application Ser. No. 15/355,234, filed on Nov. 18, 2016, now U.S. Pat. No. 10,716,934, the contents of which are hereby incorporated in their entirety.

BACKGROUND

Field of the Invention

The present invention relates generally to hearing prostheses.

Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. An auditory brainstem stimulator is another type of stimulating auditory prosthesis that might also be proposed when a recipient experiences sensorineural hearing loss due to damage to the auditory nerve.

SUMMARY

In one aspect, a method is provided. The method comprises: selecting, from electrodes implanted in a recipient of an electrically-stimulating hearing prosthesis, one or more candidate electrodes for possible deactivation; subjectively assessing a contribution of each of the one or more candidate electrodes to speech perception by the recipient; and generating, based on the subjective assessment, a final electrode set for use in subsequent hearing rehabilitation operations, wherein the final electrode set comprises a subset of the electrodes implanted in the recipient.

In another aspect, a method for selection of a set of active electrodes in an electrically-stimulating hearing prosthesis that includes a plurality of electrodes implanted in a recipient is provided. The method comprises: performing a pruning process to determine a subset of the plurality of electrodes for possible deactivation; performing a recipient-directed subjective evaluation of each electrode in the subset of the plurality of electrodes for possible deactivation; and determining, based on the subjective evaluation, the set of active electrodes for subsequent use in the electrically-stimulating hearing prosthesis.

In another aspect, a method is provided. The method comprises: measuring at least one monopolar stimulation threshold for each of a plurality of electrodes implanted in a recipient; measuring at least one focused stimulation threshold for each of the plurality of electrodes; and computing, for each of the plurality of electrodes, a threshold disparity value indicating a difference between the at least one monopolar stimulation threshold and the at least one focused stimulation threshold for the corresponding electrode.

BRIEF DESCRIPTION OF THE DRAWINGS

Embodiments of the present invention are described herein in conjunction with the accompanying drawings, in which.

DETAILED DESCRIPTION

Presented herein are techniques for the determination/selection of a set of electrodes for use in an electrically-stimulating auditory/hearing prosthesis. More specifically, an electrically-stimulating hearing prosthesis includes a plurality of electrodes implanted in a recipient. Based, at least in part on a recipient's subjective preferences, one or more of these electrodes may be deactivated. The remaining (i.e., non-deactivated) electrodes form a final electrode set that is subsequently used by the hearing prosthesis for subsequent hearing rehabilitation operations (i.e., to convert sounds to electrical stimulation for perception by the recipient).

There are a number of different types of electrically-stimulating hearing prostheses in which embodiments of the present invention may be implemented. However, merely for ease of illustration, the techniques presented herein are primarily described with reference to one type of electrically-stimulating hearing prosthesis, namely a cochlear implant. However, it is to be appreciated that the techniques presented herein may be used in other stimulating hearing prosthesis, such as auditory brainstem stimulators, electro-acoustic hearing prostheses, bimodal hearing prostheses, etc.

Figure 1A:
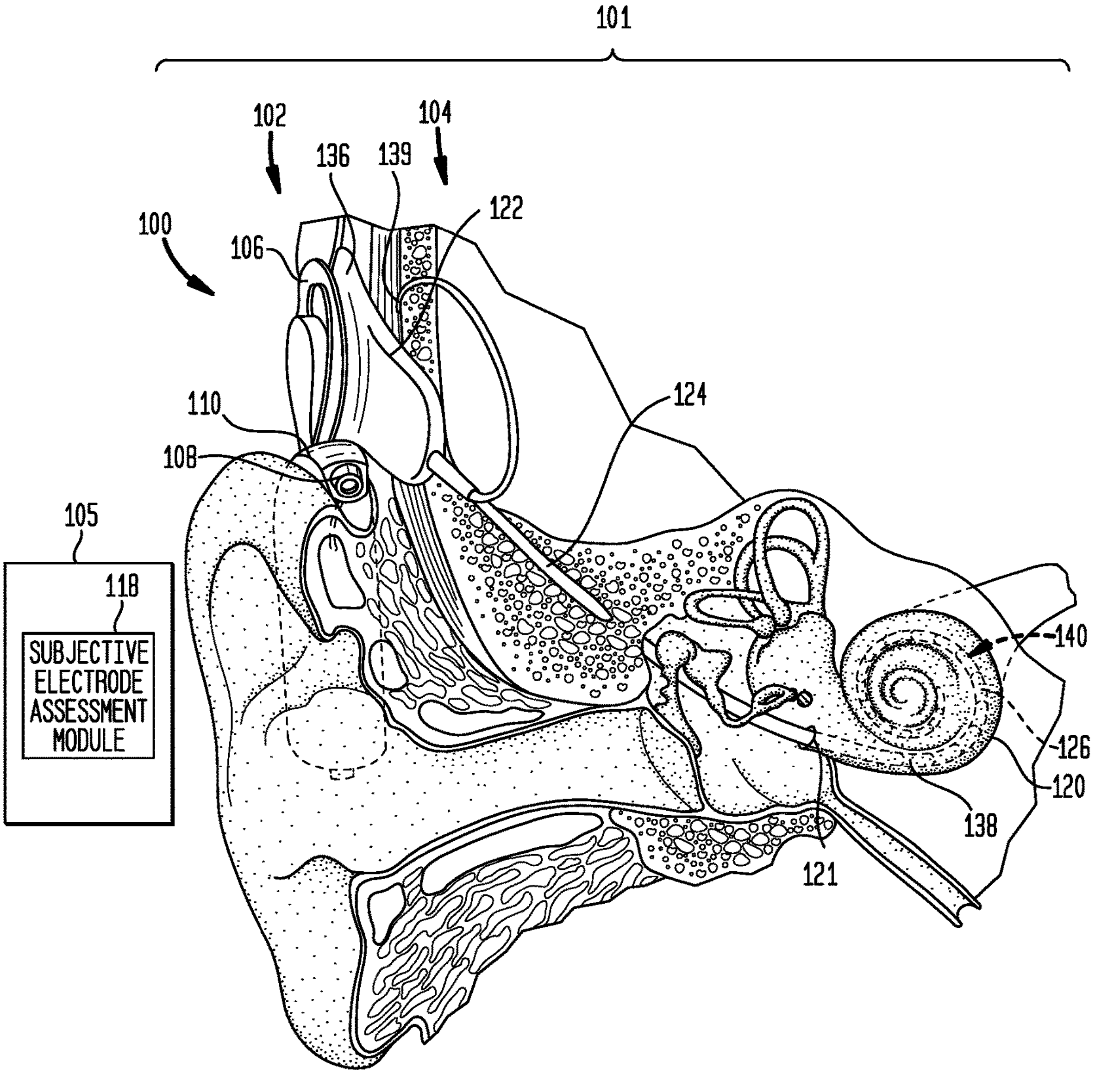
FIG. 1A is a schematic diagram of a cochlear implant system in accordance with embodiments presented herein.

FIG. 1A is schematic diagram of an exemplary cochlear implant system 101 configured to implement embodiments of the present invention. The cochlear implant system 101 comprises a cochlear implant 100 and an external device 105. The external device 105 is a computing device, such as a computer (e.g., laptop, desktop, tablet), mobile phone, remote control unit, etc. As described further below, the external device 105 comprises a subjective electrode assessment module 118 that, as described further below, is configured to facilitate subjective assessment of electrodes for deselection and to generate one or more preferred electrode sets based on the subjective assessment. Also as described further below, a selected one of these one or more preferred electrode sets may, after further objective evaluation, be selected as a final electrode set for subsequent use by the cochlear implant 100 for hearing rehabilitation operations.

The cochlear implant 100 includes an external component 102 and an internal/implantable component 104. The external component 102 is configured to be directly or indirectly attached to the body of a recipient, while the implantable component 104 is configured to be subcutaneously implanted within the recipient (i.e., under the skin/tissue of the recipient).

The external component 102 comprises a sound processing unit 110, an external coil 106, and, generally, a magnet (not shown in FIG. 1A) fixed relative to the external coil 106. The external coil 106 is connected to the sound processing unit 110 via a cable 134. The sound processing unit 110 comprises one or more sound input elements 108 (e.g., microphones, audio input ports, cable ports, telecoils, a wireless transceiver, etc.), a wireless transceiver 114, a sound processor 112, and a power source 116. The sound processing unit 110 may be, for example, a behind-the-ear (BTE) sound processing unit, a body-worn sound processing unit, a button sound processing unit, etc.

Figure 1B:
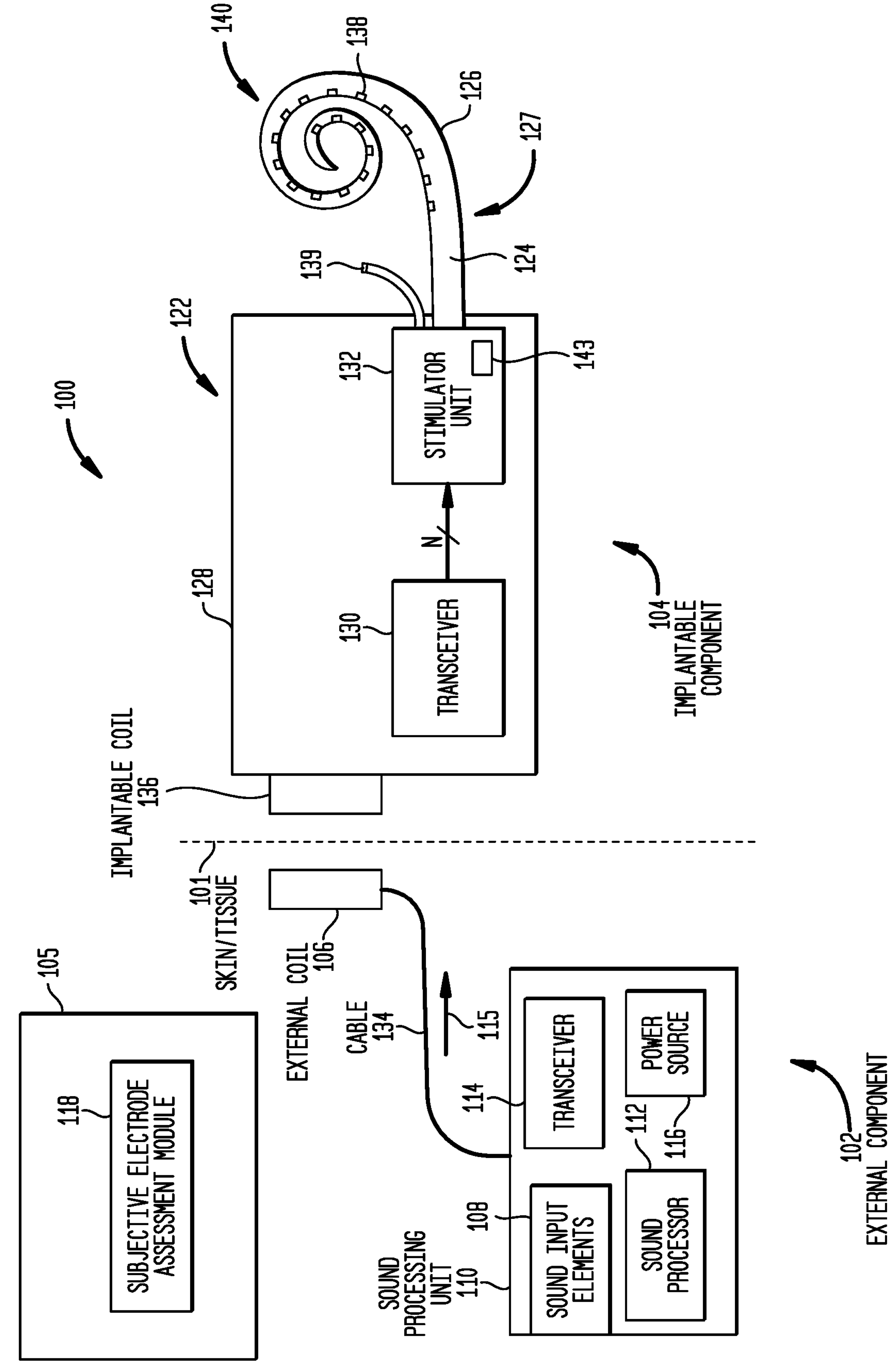
FIG. 1B is a block diagram of the cochlear system of FIG. 1A.

As shown in FIG. 1B, the implantable component 104 comprises an implant body (main module) 122, a lead region 124, and an elongate intra-cochlear stimulating assembly 126. The implant body 122 generally comprises a hermetically-sealed housing 128 in which an internal transceiver unit (transceiver) 130 and a stimulator unit 132 are disposed. The implant body 122 also includes an internal/implantable coil 136 that is generally external to the housing 128, but which is connected to the transceiver 130 via a hermetic feedthrough (not shown in FIG. 1B). Implantable coil 136 is typically a wire antenna coil comprised of multiple turns of electrically insulated single-strand or multi-strand platinum or gold wire. The electrical insulation of implantable coil 136 is provided by a flexible molding (e.g., silicone molding), which is not shown in FIG. 1B. Generally, a magnet is fixed relative to the implantable coil 136.

Elongate stimulating assembly 126 is configured to be at least partially implanted in the recipient's cochlea 120 (FIG. 1A) and includes a plurality of longitudinally spaced intracochlear electrical stimulating contacts (electrodes) 138 that collectively form a contact or electrode array 140 for delivery of electrical stimulation (current) to the recipient's cochlea.

Stimulating assembly 126 extends through an opening 121 in the cochlea (e.g., cochleostomy, the round window, etc.) and has a proximal end connected to stimulator unit 132 via lead region 124 and a hermetic feedthrough (not shown in FIG. 1B). Lead region 124 includes a plurality of conductors (wires) that electrically couple the electrodes 138 to the stimulator unit 132.

Returning to external component 102, the sound input element(s) 108 are configured to detect/receive input sound signals and to generate electrical input signals therefrom. The sound processor 112 is configured execute sound processing and coding to convert the electrical input signals received from the sound input elements into output signals that represent electric (current) stimulation for delivery to the recipient. That is, as noted, the electro-acoustic hearing prosthesis 100 operates to evoke perception by the recipient of sound signals received by the sound input elements 108 through the delivery of electrical stimulation signals to the recipient. The output signals representative of electrical stimulation are represented in FIG. 1B by arrow 115.

The output signals 115 are, in the examples of FIGS. 1A and 1B, encoded data signals that are sent to the implantable component 104 via external coil 106. More specifically, the magnets fixed relative to the external coil 106 and the implantable coil 136 facilitate the operational alignment of the external coil 106 with the implantable coil 136. This operational alignment of the coils enables the external coil 106 to transmit the encoded data signals, as well as power signals received from power source 116, to the implantable coil 136. In certain examples, external coil 106 transmits the signals to implantable coil 136 via a radio frequency (RF) link. However, various other types of energy transfer, such as infrared (IR), electromagnetic, capacitive and inductive transfer, may be used to transfer the power and/or data from an external component to an implantable component and, as such, FIG. 1B illustrates only one example arrangement.

In general, the encoded data and power signals are received at the transceiver 130 and are provided to the stimulator unit 132. The stimulator unit 132 is configured to utilize the encoded data signals to generate electrical stimulation signals (e.g., current signals) for delivery to the recipient's cochlea via one or more electrodes 138. In this way, cochlear implant 100 electrically stimulates the recipient's auditory nerve cells, bypassing absent or defective hair cells that normally transduce acoustic vibrations into neural activity, in a manner that causes the recipient to perceive one or more components of the received sound signals.

Figure 1C:
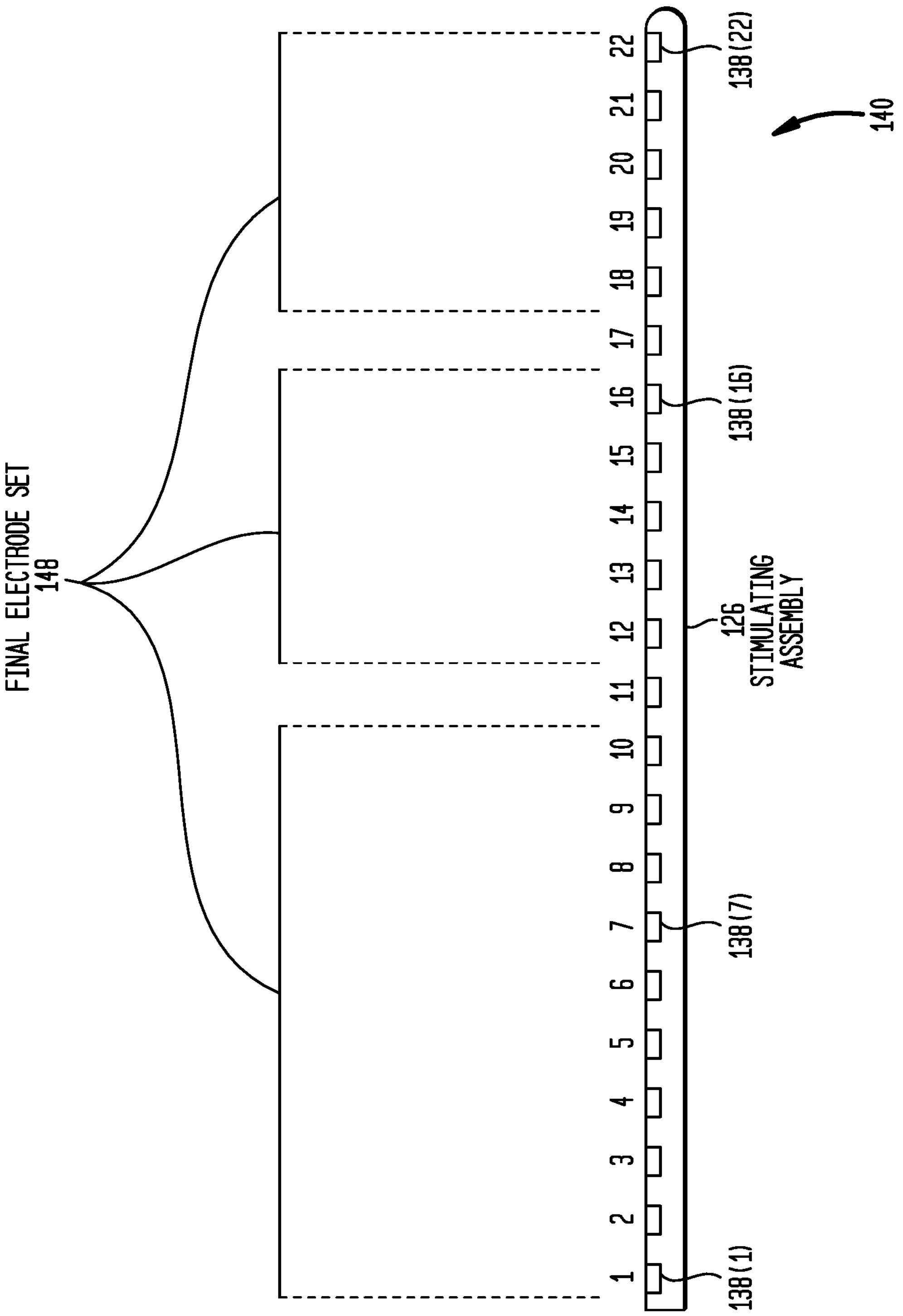
FIG. 1C is a schematic diagram of an intra-cochlear stimulating assembly configured for use in the cochlear implant system of FIG. 1A.

FIG. 1C illustrates a more detailed view of a portion of the stimulating assembly 126 comprising the array 140 of electrodes 138. FIG. 1C illustrates a specific arrangement in which the stimulating assembly 126 comprises twenty-two (22) electrodes. As such, the electrodes are labeled in FIG. 1C as electrodes 138(1) through 138(22), where electrode 138(1) is the most basal/proximal electrode and electrode 128(22) is the most distal/apical contact. As noted, the stimulating assembly 126 may also include or operate with an extra-cochlear electrode (ECE) 139 that is positioned outside of the recipient's cochlea. For ease of illustration, the extra-cochlear electrode has been omitted from FIG. 1C.

Because the cochlea is tonotopically mapped, that is, partitioned into regions each responsive to stimulus signals in a particular frequency range, acoustic frequencies are allocated to one or more electrodes 138 of the stimulating assembly 126 that are positioned close to the region that would naturally be stimulated in normal (acoustic) hearing. As such, processing channels of the sound processor (i.e., specific frequency bands with their associated signal processing paths) are each mapped to a group one or more electrodes to stimulate a selected population of cochlea nerve cells, sometimes referred to as target nerve populations or target neurons. One or more electrodes mapped to a processing channel of the sound processor are referred to herein as a "stimulation channel." That is, a stimulation channel is made up of a single or multiple electrodes stimulated (with or without a far field return contact) and the various stimulation channels are selectively used for hearing rehabilitation (i.e., for delivery of electrical to evoke perception of sound signals).

In conventional arrangements, all of the electrodes 138(1)-138(22) are used to deliver electrical stimulation to the recipient during hearing rehabilitation operations (i.e., all of the electrodes 138(1)-138(22) are mapped to one or more sound processor channels). However, it has been discovered that, in certain circumstances, the electrical stimulation delivered via one or more of the electrodes 138(1)-138(22) may not effectively stimulate the target nerve cells (i.e., may not evoke a desired response from the nerve cells). The ineffectiveness of the electrical stimulation may be caused by a number of different issues, such as physiological abnormalities (e.g., auditory nerve neuropathy, the presence of a dead region where the nerve cells are dead and non-responsive, etc.), an improper positioning of the stimulating assembly 126 within the cochlea (e.g., the electrodes 138 are spaced too far from the target nerve cells), etc.

If electrical stimulation delivered via one or more of the electrodes 138(1)-138(22) is ineffective, then the stimulation does not serve a clinical purpose and may be problematic. For example, ineffective stimulation may waste power, interfere with stimulation delivered to other nerve cells, misrepresent sounds, etc. As such, it may be desirable to deactivate electrodes that deliver ineffective stimulation and/or other electrodes such that those electrodes are not used during hearing rehabilitation operations. Presented herein are techniques for identifying electrodes that are candidates for deactivation and for subjectively assessing the effects of deactivation of these candidate electrodes. In certain examples, the techniques presented herein use automated intelligence to identify the candidate electrodes and allow the recipient to subjectively assess a contribution of these candidate electrodes to speech perception and, accordingly, what effect the deactivation of these candidate electrodes would have on speech understanding.

Based, at least in part, on the recipient's subjective assessment, a final electrode set (i.e., a subset of the plurality of electrodes 138(1)-138(22) that excludes one or more electrodes) is determined for the recipient. This final electrode set is then mapped to the various sound processor channels for use in hearing rehabilitation operations. As used herein, "deactivation" of an electrode means that the electrode is excluded (functionally) from use in delivering stimulation to a recipient.

FIG. 1C illustrates an example final electrode set 148 that may be determined through the techniques presented herein. As shown, final electrode set 148 excludes electrodes 138(11) and 138(17). It is to be appreciated that the final electrode set 148 that omits electrodes 138(11) and 138(17) is merely illustrative.

FIGS. 1A and 1B illustrate an arrangement in which the cochlear implant 100 includes an external component. However, it is to be appreciated that embodiments of the present invention may be implemented in cochlear implant systems, hearing prostheses, etc. having alternative arrangements. For example, embodiments of the present invention may also be implemented with a totally implantable cochlear implant or other totally implantable tissue-stimulating device. A totally implantable tissue-stimulating device is a medical device in which all components of the device are configured to be implanted under the skin/tissue of a recipient. Because all components are implantable, the totally implantable tissue-stimulating device operates, for at least a finite period of time, without the need of an external device. In such embodiments, an external device can be used to, for example, charge the internal power source (battery). It is also to be appreciated the embodiments presented herein may be implemented in other types of electrically-stimulating hearing prostheses, such as auditory brainstem implants, electro-acoustic hearing prostheses, etc.

Figure 2:
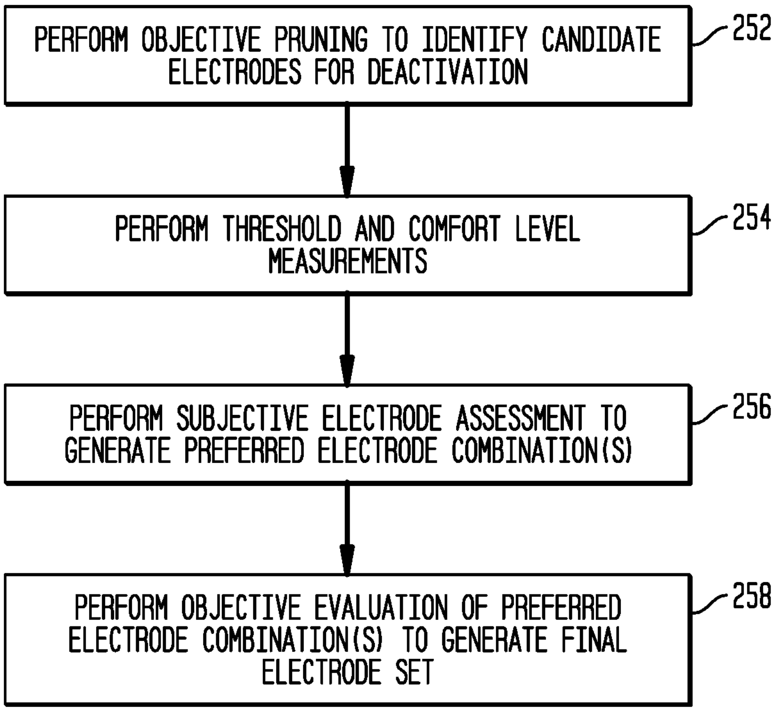
FIG. 2 is a flowchart of a method in accordance with embodiments of the present invention.

FIG. 2 is a flowchart of a method 250 in accordance with the embodiments presented herein for determining a final electrode set based, at least in part, on a recipient's subjective assessment of electrode deactivations. For ease of illustration, method 250 will be described with reference to the cochlear implant 100 of FIGS. 1A-1C.

Method 250 begins at 252 where a "pruning" process is performed to identify one or more of the electrodes 138 that may be candidates for deactivation. That is, at 252 an initial pruning analysis/process is applied to the full array of electrodes in order to identify electrodes that may be good candidates for elimination (deactivation). The general goal of this pruning process is to speed the subsequent phases (i.e., the subjective electrode assessment process). The pruning is applied to the full array of electrodes with the intention that only a limited subset will be identified as candidates for deactivation, as enabling access to all of the electrodes may be inefficient (since not all electrodes are candidates for deactivation), as well as burdensome. By limiting the analysis to only the candidate electrodes, rather than all, electrodes, the subsequent subjective assessment will require fewer subjective comparisons.

The set of candidate electrodes for deactivation, or more simply candidate electrodes, may be identified in number of different manners. In certain embodiments, the pruning process is substantially automated and is based on objective measurements of the response of the auditory nerve to stimulation by each electrode. In one form, this includes a comparison of monopolar stimulation thresholds and focused-field (focused) stimulation thresholds, such as phased array or bipolar stimulation thresholds. A disparity between monopolar and focused field stimulation thresholds correspond to regions with undesirable nerve-electrode separation and/or unhealthy neural areas.

More specifically, in these embodiments, a selected one of the electrodes 138 is used, during a first time period, to deliver monopolar stimulation to a region of the cochlea. With a cochlea implant, such as cochlear implant 100, monopolar stimulation refers to a stimulation paradigm where the current is "sourced" via one or more of the intra-cochlea electrodes 138, but the current is "sunk" by an electrode outside of the cochlea, sometimes referred to as the extra-cochlear electrode (ECE) 139 (FIGS. 1A and 1B). In response to the delivery of the monopolar stimulation, one or more other intra-cochlear electrodes 138 (i.e., electrodes that are not used to source the current) and the integrated amplifiers 143 (FIG. 1B) of the cochlear implant 100 are used to record the resulting monopolar stimulation thresholds (e.g., the electrically evoked compound action potential (ECAP) thresholds evoked by monopolar stimulation are determined using, for example, the neural response telemetry (NRT) capabilities of the cochlear implant 100). The ECAP threshold is the minimum current level required to evoke a measurable neural response.

In one example, groups of one or more monopolar stimulation signals are sequentially presented at a selected electrode with increasing levels and the measurements are performed after each group of monopolar stimulation signals are delivered. Using these measurements, the monopolar stimulation thresholds can be determined. Monopolar stimulation thresholds are determined for a plurality, and potentially all, of the electrodes 138.

Before or after the delivery of the monopolar stimulation and measurement of the monopolar stimulation threshold, the same selected electrode 138 is also used during a second time period to deliver focused stimulation to a region of the cochlea. With a cochlea implant, such as cochlear implant 100, focused stimulation refers to a stimulation paradigm where the current is "sourced" via one or more of the intra-cochlea electrodes 138, and is "sunk" by one or more other proximate intra-cochlear electrodes. In response to the delivery of the focused stimulation, one or more other electrodes 138 (i.e., electrodes that are not used to source or sink the current) and the integrated amplifiers 143 (FIG. 1B) of the cochlear implant 100 are used to record the resulting stimuli thresholds, referred to herein as focused stimuli thresholds.

In one example, groups of one or more focused stimulation signals are sequentially presented at a selected electrode with increasing levels and the measurements are performed after each group of focused stimulation signals are delivered. Using these measurements, the focused stimulation thresholds can be determined. Focused stimulation thresholds are determined for a plurality, and potentially all, of the electrodes 138.

As noted, the monopolar and the focused stimulation thresholds determined for an electrode are compared to one another in order to determine any significant disparities there between. This comparison results in the generation of a "threshold disparity value" for the corresponding electrode. If one or more disparities of sufficient importance are identified (e.g., the threshold disparity value is sufficiently large), then the selected electrode (i.e., the electrode that was used to source both the monopolar and the focused stimulation) is identified as a candidate electrode for deactivation as the selected electrode is likely associated with one or more of an undesirable nerve-electrode separation or an unhealthy neural area.

When utilizing the above objective pruning approach, there are two variables that are defined a priori: (1) the threshold disparity value that triggers the electrode to become a candidate electrode, and (2) the number of electrodes to deactivate. These two variables may be determined, for example, experimentally. The decision to deactivate electrodes based on threshold disparity values should ensure that sufficient electrodes remain to provide sufficient spectral granularity of sound. Because the two variables are interrelated, certain examples set the level at which a threshold disparity value will trigger a potential deactivate such that no more than half the electrodes in the array can be deactivated. Moreover, certain embodiments enforce a condition whereby no more than three electrodes are deactivated.

A substantially automated approach that utilizes a comparison of behavioral monopolar and focused stimuli thresholds to identify candidate electrodes is an example of one implementation of the pruning process. In other embodiments, a computerized tomography (CT) scan or other imaging technique can be used to assess the health of the nerve cells and/or the distance between the nerve cells and the various electrodes 138 and, accordingly, identify candidate electrodes for deactivation. That is, electrodes that are associated with (i.e., positioned in proximity to) unhealthy areas of nerve cells and/or are improperly positioned a distance away from the nerve cells are identified as candidates for pruning.

As noted, the pruning process at 252 is performed to identify electrodes 138 that may be candidates for deactivation. In accordance with certain embodiments presented herein, the process at 252 may also include generating a gradation of the candidate electrodes, such that some candidates have a higher chance of deactivation than others. In general, the gradation assigned to an electrode indicates a confidence that the electrode is likely delivering ineffective stimulation. In one form, the candidate electrodes are graded or ranked relative to one another and the likelihood of deactivation is relative to each threshold disparity value. For example, a set of threshold disparity values may be determined as 0, 5, 10, and 20 for electrodes 138(1), 138(2), 138(3), and 138(4), respectively. In this example, the likelihood of deactivation is relative to each threshold disparity value, such that in this example, electrode 138(1) stands a low chance of being deactivated, while electrode 138(4) stands a high chance of being deactivated. The gradation may be associated with weighting values (weights) that could be used in the subsequent subjective assessments and/or objective evaluations. The weighting values may be valuable if subsequent phases reevaluate the selection of deactivated electrodes.

Returning to the example of FIG. 2, electrically-stimulating hearing prostheses, such as cochlear implant 100, operate by delivering electrical stimulation to the recipient within a window/range of electrical amplitudes (current levels). In particular, if the amplitude of the electrical stimulation signals is too low, then the associated sounds used to generate the electrical stimulation signals will not be perceived by the recipient (i.e., the stimulation signals will either not evoke a neural response in the cochlea or evoke a neural response that cannot be perceived by the recipient). Conversely, if the amplitude of the electrical stimulation signals is too high, then the associated sounds used to generate the electrical stimulation signals will be perceived as too loud or uncomfortable by the recipient. As such, electrical stimulation signals are generally delivered between a lower limit, referred to as a "threshold" or more simply "T" level, at which the associated sound signals are barely audible to the recipient, and an upper limit, referred to as a "most comfortable," "comfort," or more simply "C" level, above which the associated sound signals are uncomfortably loud to the recipient. The difference in electrical amplitudes between the threshold level and the comfort level is referred to herein as the "dynamic range" of the electrode.

The method 250 includes a threshold and comfort level measurement process at 254 where the behavioral threshold and comfort levels are measured for the remaining subset of electrodes that have not been identified (flagged) as candidate electrodes for deactivation, or electrodes that have low assigned weights (in embodiments that use the grading operations described above). That is, 254 includes the measurement of a recipient's behavioral response to stimulation at each electrode in order to determine the threshold and comfort levels for all of the remaining electrodes. The threshold and comfort levels are measured for all of the remaining electrodes because the following phase(s) of the method 250 allow a recipient to experience different electrode combinations and judge the subjective value of keeping or deactivating the questionable electrode candidates. That is, any of the remaining electrodes may be utilized during the subsequent electrode assessment phase to deliver stimulation to the cochlea. In order to safely and effectively deliver stimulation, the threshold and comfort levels should first be determined. Weighting, when present, may have a role in the inclusion or elimination of electrodes to sets presented to recipients.

The recipient's threshold and comfort levels are measured using various series of signals at specific frequencies/frequency ranges (e.g., different "beeps"). For example, a series of beeps is iteratively delivered to a recipient with increasing loudness via a selected electrode. After each iteration, the recipient's response (e.g., subjective or objective) is obtained. Based on the response, a determination can be made as to whether the beep was too soft (i.e., below the recipient's threshold level), too loud (i.e., above the recipient's comfort level), or between the recipient's threshold and comfort levels. Through the use of a number of iterations, frequencies, and varying loudnesses, the recipient's threshold and comfort levels for the remaining subset of electrodes 138 (i.e., the electrodes not identified as candidates for pruning) are determined.

Figure 3:
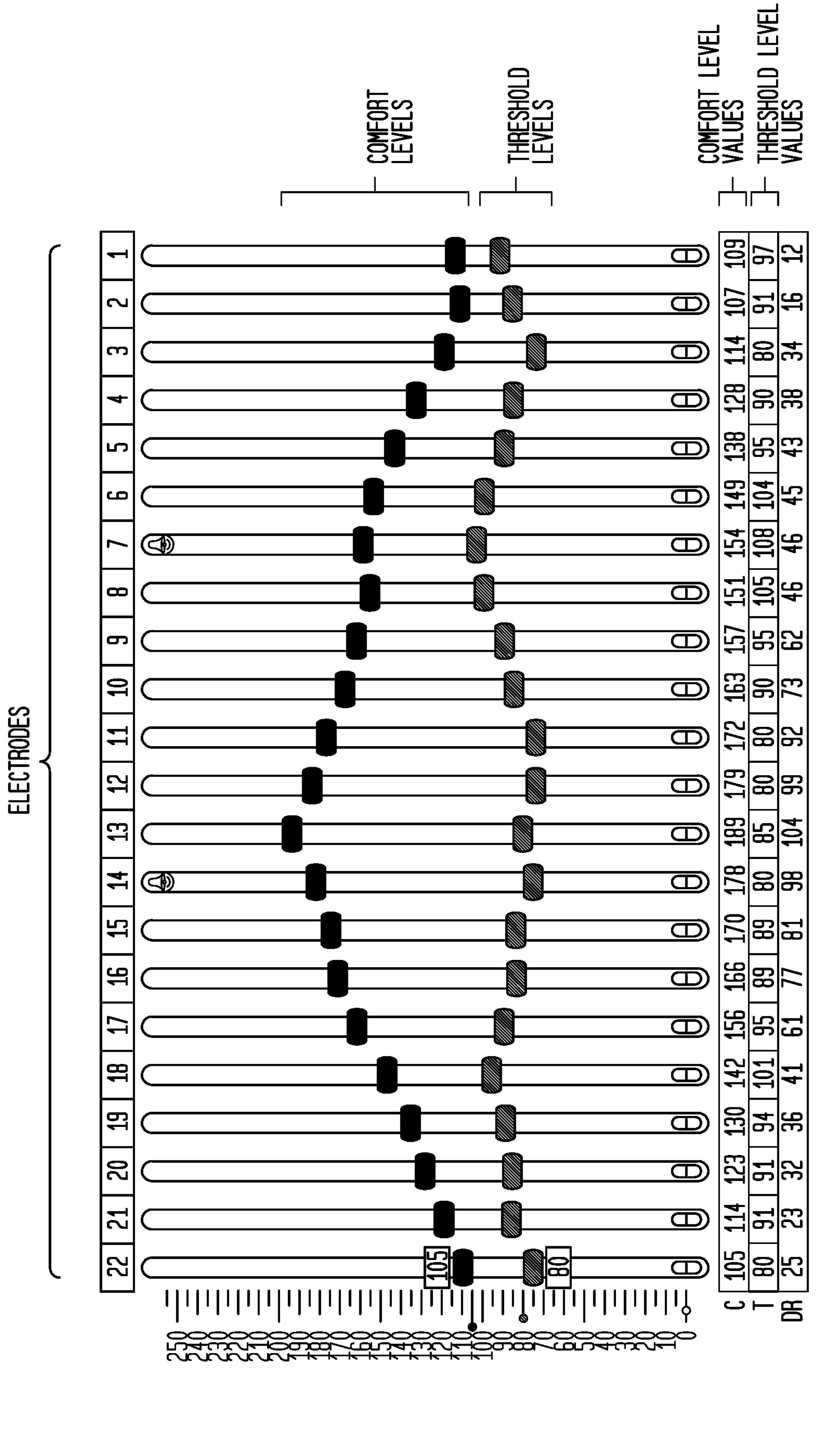
FIG. 3 is a screen capture of a fitting system display which illustrates behavioral measurement threshold and comfort levels determined for a recipient of a cochlear implant.

A screen capture of a fitting system display which illustrates behavioral measurement threshold and comfort levels is shown in FIG. 3. In this example, a clinician increases each electrode stimulation level until the recipient indicates that he/she hears the sound represented by the delivered stimulation. The stimulation level that evokes the hearing perception is the behavioral threshold level. The clinician then continues to increase the stimulation level until the recipient judges the level to be louder than he/she can tolerate for an extended period of time. This level is then considered the behavioral comfort level. As noted above, the difference between the comfort level and the threshold is the dynamic range of the electrode. FIG. 3 illustrates artificial threshold and comfort levels that may be measured in a clinical environment.

In certain examples, a clinician may double check electrode threshold and comfort levels by sweeping one electrode at a time, or by sweeping groups of electrodes. In addition, the clinician may activate the electrodes and presents sounds to the recipient (i.e., "goes live") to ensure the comfort levels are set correctly (i.e., no single electrode seems too loud).

As noted above, method 250 illustrates an example where an initial pruning process 252 is performed to identify one or more of the electrodes 138 that may be candidates for deactivation. In certain embodiments, the initial pruning process 252 is omitted and, instead, the pruning process forms part of the operations of 254. More specifically, as shown in FIG. 3, there may be great disparities between the dynamic ranges determined for different electrodes across the array. It has been determined that electrodes having a small dynamic range may correlate to problematic areas of the cochlea (e.g., undesirable nerve-electrode separations, unhealthy neural areas, etc.). Therefore, in certain embodiments, the pruning process includes an evaluation of the dynamic ranges determined for the electrodes. Electrodes that have a sufficiently small dynamic range (e.g., dynamic ranges smaller than a selected threshold), or the electrodes that have the relatively smallest dynamic ranges (e.g., the 3, 5, 7, etc. smallest dynamic ranges) are selected as the candidates for deactivation.

Returning to the specific example of FIG. 2, the method 250 also includes a subjective electrode assessment at 256 where the recipient's subject feedback is used to evaluate the candidate electrodes and, ultimately, generate one or more preferred electrode sets. The subjective electrode assessment is intended to functionally test different electrode combinations in which one or more of the candidate electrodes are deactivated in the presence of speech. That is, subjective electrode assessment is an iterative process where the recipient is exposed to phonemically rich and balanced speech in an effort to ensure all relevant spectral (phonetic) components are encountered by the recipient when using different combinations of electrodes that omit one or more of the candidate.

More specifically, as noted above, as a result of the operations at 254, or as a result of the operations of 252 and 254, candidate electrodes for deactivation are identified/determined. Therefore, at this point there are two different groups of electrodes, namely those believed to be delivering functionally appropriate stimulation (referred to as core electrodes) and those deemed to be good candidates for deselection/deactivation (referred to as candidate electrodes). The subjective electrode assessment at 256 combines the core electrodes with different incarnations of the candidate electrodes (i.e., different groups of core and candidate) into different test combinations. Each test combination of electrodes is used to deliver phonemically rich test speech to the recipient. Recipients are then asked to compare/judge the results of the different test combinations (i.e., subjective assess the test combinations relative to another in terms of how well they each represent the test speech).

This subjective electrode assessment process can take many forms. For instance, in one form the different test combinations of candidate and core electrodes are presented as buttons on a user interface (e.g., in a matrix) and the user is free to sample each one at his/her leisure (e.g., pressing down on any option plays a test speech sample processed with the selected combination). Depending on how the eliminating parameters (dynamic range cut offs) were defined, such a button matrix incorporating the test combinations (core+candidate) set can vary greatly in size.

In other embodiments, a competitive elimination process (e.g., competitive elimination bracket approach or paired comparison approach) can be used to subjectively assess the different test combinations of candidate and core electrodes. In these embodiments, two different test combinations are selected to "compete" against one another. For example, the recipient is presented with speech using a first test combination, and then is presented with the same speech using a second test combination. The recipient then selects the test combination that he/she prefers. The selected test combination is saved for further "competitions," while the non-selected test combination may be eliminated. In certain examples, double or even triple elimination rules can be enforced for better reliability and for smaller gross comparison sets. Through multiple head-to-head competitions, the competitive elimination process results in the selection of a preferred electrode combination or, in certain examples, a few preferred electrode combinations.

In alternative embodiments, a tabu list approach can be used to facilitate the subjective assessment of the different test combinations of candidate and core electrodes. In such embodiments, rather than using the traditional double elimination tournament style approach (as discussed above), recipients perform a paired comparison between two different electrode sets that each include different combinations of candidate and/or core electrodes. A running tabu list is kept in memory such that every time an electrode set is rejected (i.e., is identified as the less preferred of two sets), the rejected electrode set is placed on the tabu list. After every paired judgment, two new electrode sets are selected at random from the full population of all possible electrode sets and then subjectively compared against each other. If an electrode set is rejected twice (i.e., appears on the tabu list twice), then it is removed from the full population of possibilities. This would be the double elimination configuration, but a triple or other elimination rule could also be enforced instead.

In certain embodiments, the subjective electrode assessment process can be completed without the presence of a support individual (talker) by providing recorded test speech accompanied by an on-screen text representation or other feedback mechanism that enables the recipient to select or grade the results of stimulation delivered using a test combination. Furthermore, although the subjective electrode assessment process is subjective in nature, it may be advantageous to incorporate a conversational speech performance test (e.g., AzBio, HINT, etc.) or phoneme confusion matrix.

As noted above, the subjective electrode assessment results in the identification of one or more combinations of electrodes (e.g., core and candidate electrodes) which the recipient has identified as being preferred by the recipient (i.e., preferred electrode combinations). At 258, a final objective assessment of the one or more preferred electrode combinations is performed to ensure that the one or more preferred electrode combinations expose the recipient to the full range of spectral information. For example, certain electrodes, such as electrodes that present high frequency sounds, may sound terrible to a recipient. As such, the recipient may select preferred electrode combinations in which these higher frequency electrodes are deactivated. However, such electrodes selected by the recipient for deactivation may actually be important for understanding speech. As such, in the final objective assessment 258, the recipient's preferences can be overridden or modified, as needed, to ensure the recipient is exposed all of the desired spectral information.

At the end of 258, a final electrode set is determined for the recipient. This final electrode set comprises a subset of the plurality of electrodes 138 that are to be used by the hearing prosthesis for hearing rehabilitation operations (e.g., mapped to sound processing channels).

The objective assessment at 258 may include, for example, a spectral ripple test to determine which spectral components are underserved (not sufficiently presented) by the preferred electrode combination(s). Furthermore, if a performance assessment was not included as part of 256, then it can be performed in 258.

In certain examples, the operations at 256 and 258 are iterated to avoid the variability of subjective decisions and to ensure the recipient selects the most suitable electrode combination. At each iteration, one or more control parameters (e.g., the number of electrodes that can be candidates for deactivation, the specific electrodes that can be candidates, the subjective assessment process, etc.) can be modified to skew the selection. In certain such examples, multiple different final electrode sets may be generated and compared relative to one another for selection and subsequent use by the cochlear implant 100.

In summary, FIG. 2 illustrates iterative optimization techniques to identify a final electrode set that eliminates unnecessary electrodes (i.e., electrodes that do not significantly contribute to sound perception), yet ensures the recipient receives a full range of spectral information.

In general, the techniques presented are limited in time only by the recipient, not the clinic. In particular, the operations of 252, 254, and 256 may be performed sequentially or in discrete steps. Additionally, a recipient may perform the operations of 256 many times iteratively on his/her own schedule. Additionally, the various operations at 252, 254, 256, and 258 may be performed in different environments. In general, the operations at 252, 254, and 258 are performed in a clinical environment, while the operations at 256 may be performed in the clinical or in a remote environment.

As noted above, in certain circumstances, the monopolar and the focused stimulation thresholds determined for an electrode are compared to one another in order to determine any significant disparities there between. This comparison results in the generation of a "threshold disparity value" for the corresponding electrode. This threshold disparity value can be used to identify so-called dead regions or to determine if the particular electrode is positioned far away from the nerve. As such, the threshold disparity value could be used for other clinical/diagnostic applications beyond identification of candidate electrodes.

Figure 4:
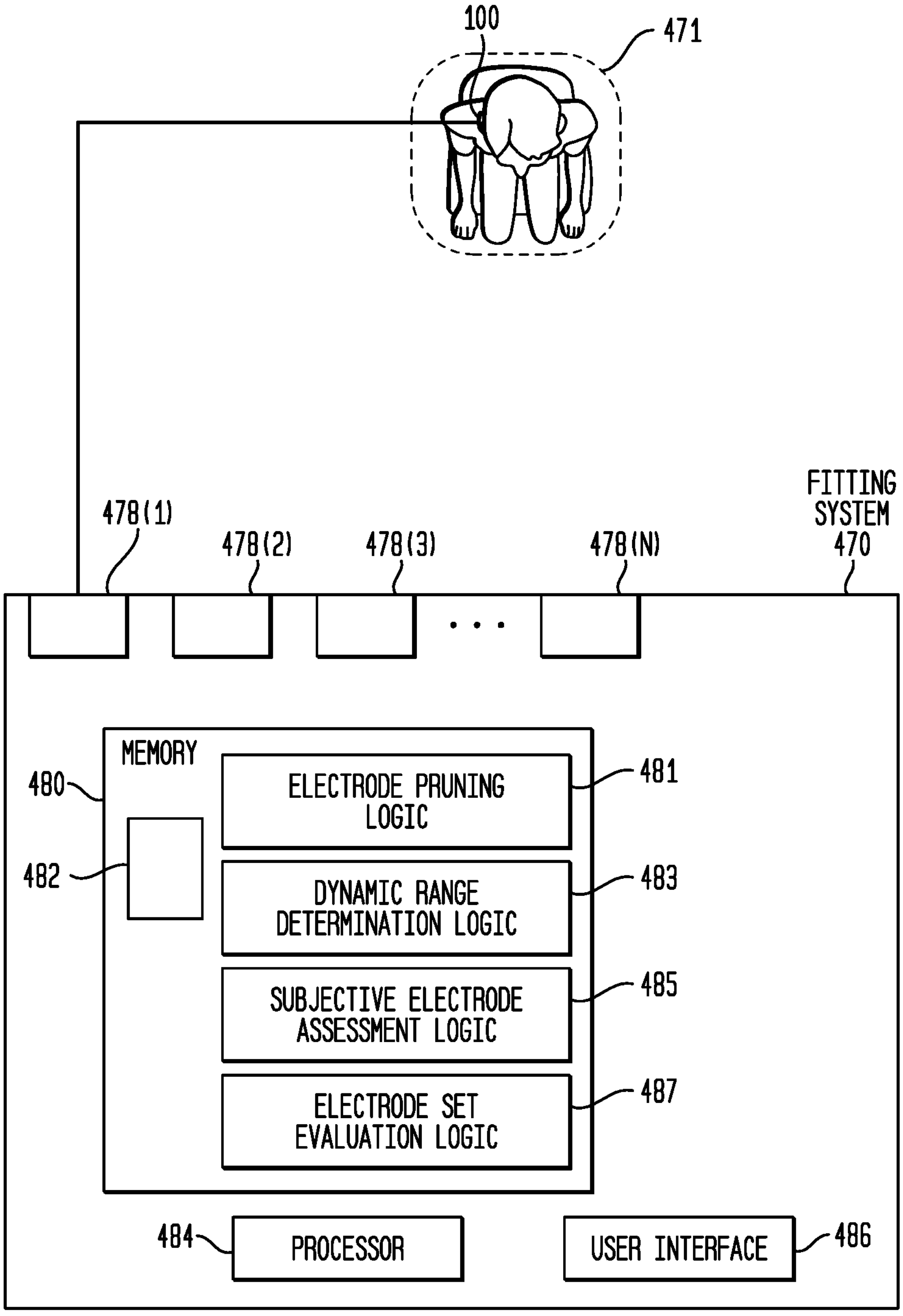
FIG. 4 is a block diagram of a fitting system configured to execute techniques in accordance with embodiments of the present invention.

FIG. 4 is block diagram illustrating an example fitting system 470 configured to perform or facilitate one or more of the operations described in FIG. 2. Fitting system 470 is, in general, a computing device that comprises a plurality of interfaces/ports 478(1)-478(N), a memory 480, a processor 484, and a user interface 486. The interfaces 478(1)-478(N) may comprise, for example, any combination of network ports (e.g., Ethernet ports), wireless network interfaces, Universal Serial Bus (USB) ports, Institute of Electrical and Electronics Engineers (IEEE) 1494 interfaces, PS/2 ports, etc. In the example of FIG. 4, interface 478(1) is connected to cochlear implant 100 having components implanted in a recipient 471. Interface 478(1) may be directly connected to the cochlear implant 100 or connected to an external device (not shown in FIG. 4) that is in communication with the cochlear implant 100. Interface 478(1) may be configured to communicate with cochlear implant 100 via a wired or wireless connection (e.g., telemetry, Bluetooth, etc.).

The user interface 486 includes one or more output devices, such as a liquid crystal display (LCD) and a speaker, for presentation of visual or audible information to a clinician, audiologist, or other user. The user interface 486 also comprises one or more input devices that include, for example, a keypad, keyboard, mouse, touchscreen, etc.

In the specific example of FIG. 4, the memory 480 comprises electrode pruning logic 481 that may be executed to generate a candidate set of electrodes for possible deactivation/deselection. In one example, data 482 representing the identified candidate set of electrodes is also stored in the memory 480 (e.g., perform the operations described above with reference to 252 of FIG. 2). The memory 480 also comprises dynamic range determination logic 483 that may be executed to determine dynamic ranges for implanted electrodes (i.e., determine threshold and comfort levels, as described above with reference to 254 of FIG. 2). In addition, memory 480 comprises, in this example, subjective electrode assessment logic 485 that may be executed to facilitate the evaluation of the candidate electrodes by the recipient and to generate one or more preferred electrode combinations (e.g., perform the operations described above with reference to 256 of FIG. 2). Finally, memory 480 comprises electrode set evaluation logic 487 that may be executed to confirm that the preferred electrode combinations are clinically acceptable and, ultimately, select or authorize a final electrode set for use by the recipient for subsequent hearing operations (e.g., perform the operations described above with reference to 258 of FIG. 2).

FIG. 4 illustrates a specific example in which a final electrode set is determined completely in the clinical environment. However, as noted above, various operations presented herein may be performed outside of the clinical environment. For example, the subjective electrode assessment may be performed directly in a remote environment, possibly without clinical oversight. In such embodiments, the subjective electrode assessment logic 485 may be omitted and, instead, will be present and executable by the cochlear implant system 101.

Additionally, also as noted above, the pruning operations to identify a candidate set of electrodes may be performed as part of the dynamic range determination. Therefore, the electrode pruning logic 481 may also be omitted in certain embodiments.

In general, memory 480 may comprise read only memory (ROM), random access memory (RAM), magnetic disk storage media devices, optical storage media devices, flash memory devices, electrical, optical, or other physical/tangible memory storage devices. The processor 484 is, for example, a microprocessor or microcontroller that executes instructions for the logic (e.g., logic 481, 483, 485, and 487) stored in the memory 480. Thus, in general, the memory 480 may comprise one or more tangible (non-transitory) computer readable storage media (e.g., a memory device) encoded with software comprising computer executable instructions and when the software is executed (by the processor 484) it is operable to perform the operations described herein.

Figure 5:
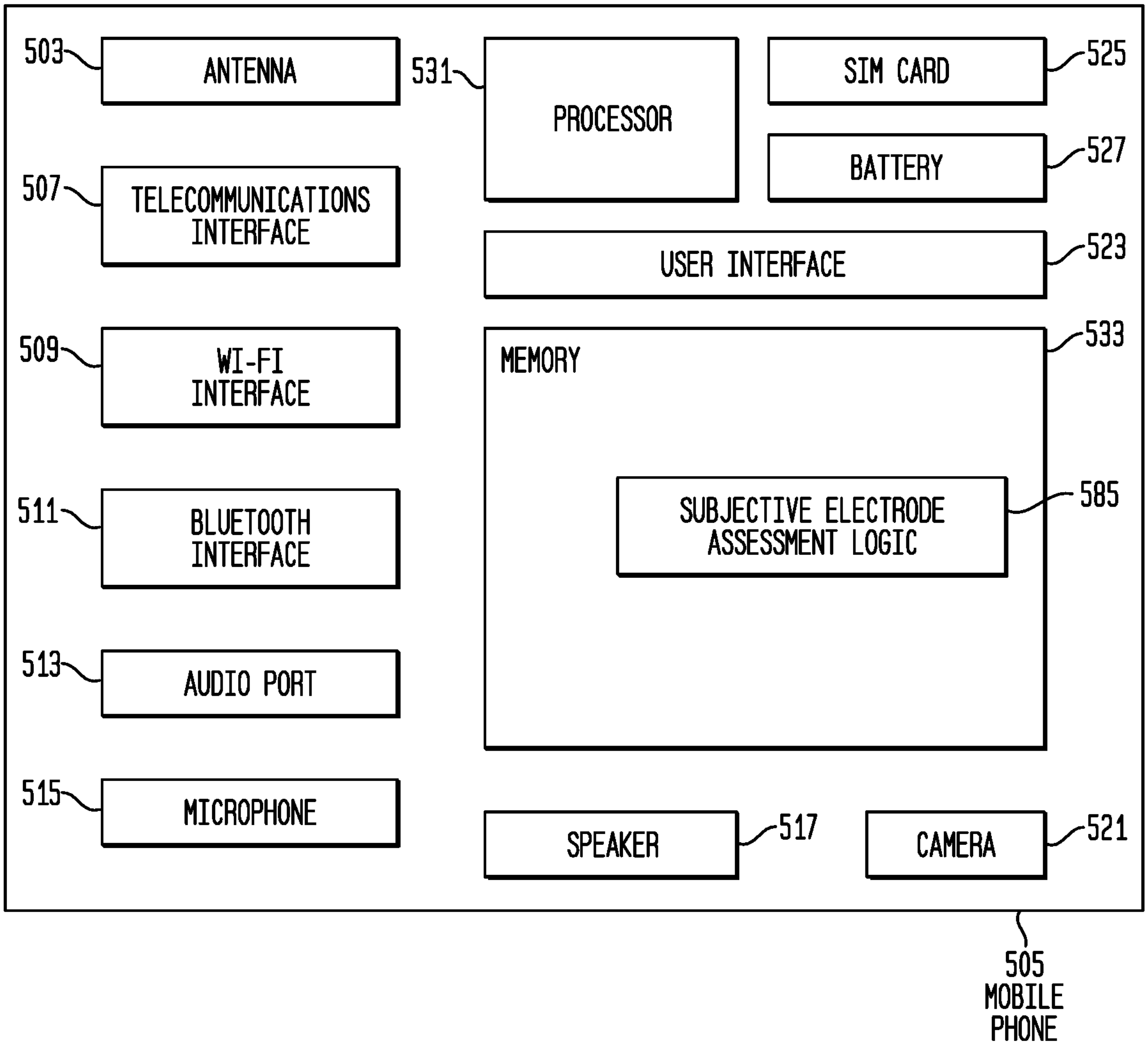
FIG. 5 is a block diagram of a computing device configured to execute techniques in accordance with embodiments of the present invention.

As noted above, certain operations described herein may performed in a remote environment using, for example, a computer, mobile phone, or other consumer electronic device forming part of a hearing prosthesis system. FIG. 5 is a block diagram of an illustrative arrangement for a mobile phone 505 in accordance with embodiments presented herein that is configured to facilitate the subjective electrode assessment of the candidate electrodes (e.g., perform the operations described above with reference to 256 of FIG. 2). It is to be appreciated that FIG. 5 is merely illustrative and that subjective electrode assessments may be performed at other devices having different arrangements than that shown in FIG. 5.

Mobile phone 505 comprises an antenna 503 and a telecommunications interface 507 that are configured for communication on a wireless communication network for telephony services (e.g., a Global System for Mobile Communications (GSM) network, code division multiple access (CDMA) network, time division multiple access (TDMA), or other kinds of networks). Mobile phone 505 also includes a wireless local area network interface 509 and an infrared (IR) or Bluetooth® interface 511. The Bluetooth® trademark is owned by the Bluetooth® SIG. The wireless local area network interface 509 allows the mobile phone 505 to exchange data or connect to the Internet using, for example, 2.5 Gigahertz (GHz) Ultra high frequency (UHF) and/or 5 GHz Super high frequency (SHF) radio waves. The Bluetooth® interface 511 enables the mobile phone 505 to wirelessly communicate (i.e., directly receive and transmit data to/from another device via a wireless connection). In certain examples, the Bluetooth® interface 511 may be used to wirelessly connect the mobile phone 505 to the cochlear implant 100 (FIGS. 1A and 1B). It is to be appreciated that the use of a wireless local area network interface in combination with a Bluetooth® interface is merely illustrative and that any other interfaces now known or later developed including, but not limited to, Institute of Electrical and Electronics Engineers (IEEE) 802.11, IEEE 802.16 (WiMAX), fixed line, Long Term Evolution (LTE), etc. interfaces may also or alternatively form part of the mobile phone 503.

Mobile phone 503 also comprises an audio port 513, one or more sound input elements, such as a microphone 519, a speaker 517, a camera 521, a user interface 523, a subscriber identity module or subscriber identification module (SIM) card 525, a battery 527, a processor 531, and a memory 533. Memory 533 comprises subjective electrode assessment logic 585 that may be executed to facilitate the subjective assessment of the candidate electrodes and to generate one or more preferred electrode combinations (e.g., perform the operations described above with reference to 256 of FIG. 2).

Memory 533 may comprise ROM, RAM, magnetic disk storage media devices, optical storage media devices, flash memory devices, electrical, optical, or other physical/tangible memory storage devices. The processor 531 is, for example, a microprocessor or microcontroller that executes instructions for the subjective electrode assessment logic 585. Thus, in general, the memory 533 may comprise one or more tangible (non-transitory) computer readable storage media (e.g., a memory device) encoded with software comprising computer executable instructions and when the software is executed (by the processor 531) it is operable to perform the corresponding operations described herein.

In general, execution of the subjective electrode assessment in the remote environment enables the person to evaluate the various combinations of electrodes at his/her own leisure and on his/her own schedule. For example, the subjective electrode assessment logic 585, when executed, can run different scenarios to "test" omitting electrodes and store the recipient feedback over an extended period of time. Performing the subjective electrode assessment outside of the clinical environment and in the environments (e.g., home, office, etc.) typically encountered by the recipient also further optimizes the selection process as the recipient's choices/preferences will inherently account for the background noises, etc. encountered by the recipient on a daily basis.

In certain examples, the user interface 523 may include a plurality of buttons, icons, or other indicators that each correspond to a speech token (e.g., word, phrase, etc.) and a test combination of electrodes. Pressing the indicator causes the cochlear implant 100 to present the speech token to the recipient using the associated test combination of electrodes. The user interface 523 may also include one or more indicators that allow the recipient to provide feedback regarding the test combination of electrodes.

Presented herein is a new approach for determining, based on a recipient's subjective preferences, which electrodes should be deactivated. That is, the techniques presented herein to identify a subset of questionable electrodes and enable a recipient to use his/her own judgment to decide which electrodes to deactivate.

Although the techniques have primarily been described above with reference to a cochlear implant, it is to be appreciated that the techniques presented herein may be used in other stimulating hearing prosthesis, such as auditory brainstem stimulators, electro-acoustic hearing prostheses, bimodal hearing prostheses, etc. For example, depending on the implementation, the techniques presented herein may be used in an electro-acoustic hearing prosthesis to valuate a recipient defined frequency transition between acoustic and electrical stimulation (i.e., evaluate the crossover frequency). An electro-acoustic hearing prosthesis is configured to deliver both acoustical stimulation and electrical stimulation to a recipient (i.e., the lower frequencies are provided by acoustic hearing and the higher frequencies are provided by electrical stimulation). Currently, the decision for assigning the low and high frequency ranges is somewhat arbitrary where, if a hearing deficit (pure tone average) is below 70 dB, then sound is provided acoustically. Otherwise, the sound is provided electrically. Self activation/deactivation as described above may be beneficial for optimizing this process.

The techniques presented herein have the advantage of potentially avoiding undesirable physical stimulation or sensation and the ability to optimize in any acoustical environment, thereby making the techniques useful for take-home use and opens the door for rehabilitative application. Furthermore, all steps and results of the procedure would be logged in memory and posted to the patient's clinician for supervision purposes.

It is to be appreciated that the above described embodiments are not mutually exclusive and that the various embodiments can be combined in various manners and arrangements.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:

selecting, from electrodes implanted in a recipient of an electrically-stimulating prosthesis, one or more candidate electrodes for possible deactivation;

assessing a contribution of each of the one or more candidate electrodes to rehabilitative effect on the recipient, wherein assessing the contribution of the one or more candidate electrodes to the rehabilitative effect on the recipient includes determining whether any of the one or more candidate electrodes deliver ineffective stimulation; and generating, based on the assessing, a final electrode set for use in subsequent operations, wherein the final electrode set comprises a subset of the electrodes implanted in the recipient in which at least one of the one or more candidate electrodes have been deactivated and excluded from use in subsequent operations.

2. The method of claim 1, wherein assessing a contribution of the one or more candidate electrodes to the rehabilitative effect on the recipient comprises:

subjectively assessing, based on recipient-provided feedback, a contribution of each of the one or more candidate electrodes to the rehabilitative effect on the recipient.

3. The method of claim 1, wherein assessing a contribution of the one or more candidate electrodes to the rehabilitative effect on the recipient comprises:

assessing a contribution of each of the one or more candidate electrodes to speech perception of the recipient to sound signals.

4. The method of claim 3, wherein assessing a contribution of the one or more candidate electrodes to the rehabilitative effect on the recipient comprises:

determining a plurality of test combinations of electrodes, wherein one or more of the test combinations includes at least one of the one or more candidate electrodes;

iteratively delivering electrical stimulation to the recipient, wherein the electrical stimulation represents test speech and each iteration is delivered using one of the plurality of test combinations;

in response to each iteration of electrical stimulation, receiving subjective feedback from the recipient that characterizes the utilized one of the plurality of test combinations; and identifying, based on the subjective feedback received from the recipient, at least one preferred electrode combination.

5. The method of claim 4, wherein generating a final electrode set includes:

performing an objective evaluation of the at least one preferred electrode combination to determine whether any spectral components are not sufficiently presented by the at least one preferred electrode combination.

6. The method of claim 1, wherein selecting the one or more candidate electrodes comprises:

selecting the one or more candidate electrodes based on objective measurements obtained from the recipient.

7. The method of claim 6, wherein selecting the one or more candidate electrodes based on objective measurements, comprises:

determining one or more monopolar stimulation thresholds for a plurality of the electrodes;

determining one or more focused stimulation thresholds for the plurality of the electrodes;

comparing, for each of the plurality of the electrodes, the one or more monopolar stimulation thresholds and the one or more focused stimulation thresholds determined for a corresponding one of the plurality of the electrodes to identify any disparities; and selecting the one or more candidate electrodes based on any disparities between the monopolar stimulation thresholds and the focused stimulation thresholds for a corresponding electrode.

8. The method of claim 1, selecting the one or more candidate electrodes comprises:

determining a dynamic range for each of a plurality of the electrodes, wherein the dynamic range comprises a difference between a behavioral threshold level and a behavioral comfort level for an electrode; and identifying, as the one or more candidate electrodes, electrodes having a dynamic range that is smaller than a predetermined threshold.

9. The method of claim 1, wherein the electrodes are implanted at a recipient's inner ear, and wherein the method further comprises:

assessing, based on a computerized image of the recipient's inner ear and the electrodes implanted in the recipient, one or more of a health of nerve cells of the cochlea or a distance between the nerve cells and the electrodes; and identifying, as the one or more candidate electrodes, electrodes positioned in proximity to unhealthy areas of nerve cells or electrodes that are improperly positioned a distance away from the nerve cells.

10. A method for selection of a set of active electrodes in an electrically-stimulating prosthesis that includes a plurality of electrodes implanted in a recipient, the method comprising:

performing a pruning process to determine a subset of the plurality of electrodes for possible deactivation;

evaluating a contribution of each electrode in the subset of the plurality of electrodes for possible deactivation to a rehabilitative effect on the recipient, wherein evaluating the contribution of each electrode in the subset of the plurality of electrodes for possible deactivation to the rehabilitative effect on the recipient includes determining whether any of the subset of the plurality of electrodes deliver ineffective stimulation; and determining, based on the evaluation, the set of active electrodes for subsequent use by the electrically-stimulating prosthesis for stimulating the recipient, wherein at least one electrode in the subset of the plurality of electrodes for possible deactivation is deactivated and excluded from use in the set of electrodes for subsequent use in the electrically-stimulating prosthesis.

11. The method of claim 10, wherein evaluating a contribution of each electrode in the subset of the plurality of electrodes for possible deactivation to the rehabilitative effect on the recipient comprises:

subjectively assessing, based on recipient-provided feedback, a contribution of each electrode in the subset of the plurality of electrodes to the rehabilitative effect on the recipient.

12. The method of claim 10, wherein evaluating a contribution of each electrode in the subset of the plurality of electrodes for possible deactivation to the rehabilitative effect on the recipient comprises:

assessing a contribution of each electrode in the subset of the plurality of electrodes to speech perception of the recipient to sound signals.

13. The method of claim 10, wherein performing the pruning process comprises:

obtaining a plurality of objective measurements via the plurality of electrodes; and determining the subset of the plurality of electrodes for possible deactivation based on the objective measurements.

14. The method of claim 13, wherein obtaining a plurality of objective measurements via the plurality of electrodes comprises:

measuring one or more monopolar stimulation thresholds for each of the electrodes; and measuring one or more focused stimulation thresholds for each of the electrodes.

15. The method of claim 14, wherein determining the subset of the plurality of electrodes for possible deactivation based on the objective measurements comprises:

comparing, for each of the plurality of electrodes, the one or more monopolar stimulation thresholds and the one or more focused stimulation thresholds measured for a corresponding one of the plurality of electrodes; and identifying, as part of the subset of the plurality of electrodes for possible deactivation, any electrodes having a disparity between the corresponding monopolar stimulation thresholds and the corresponding focused stimulation thresholds that is greater than a predetermined threshold.

16. The method of claim 10, wherein performing the pruning process comprises:

determining a dynamic range for each of a plurality of the electrodes, wherein the dynamic range comprises a difference between a behavioral threshold level and a behavioral comfort level for an electrode; and identifying, as part of the subset of the plurality of electrodes, electrodes having a dynamic range that is smaller than a predetermined threshold.

17. The method of claim 10, wherein evaluating a contribution of each electrode in the subset of the plurality of electrodes for possible deactivation to a rehabilitative effect on by the recipient comprises:

determining a plurality of test combinations of electrodes, wherein one or more of the test combinations includes at least one electrode selected from the subset of the plurality of electrodes;

iteratively delivering electrical stimulation to the recipient, wherein the electrical stimulation represents test speech and each iteration is delivered using one of the plurality of test combinations;

in response to each iteration of electrical stimulation, receiving subjective feedback from the recipient that characterizes the utilized test combination; and identifying, based on the subjective feedback received from the recipient, at least one preferred electrode combination.

18. The method of claim 17, wherein determining a set of active electrodes for subsequent use in the electrically-stimulating prosthesis further comprises:

performing an objective evaluation of the at least one preferred electrode combination to determine whether any spectral components are not sufficiently presented by the at least one preferred electrode combination.

* * * * *